(12) United States Patent
Primus

(10) Patent No.: US 7,892,342 B2
(45) Date of Patent: Feb. 22, 2011

(54) DENTAL MATERIAL

(75) Inventor: Carolyn M. Primus, Sarasota, FL (US)

(73) Assignee: DENTSPLY International, Inc., York, PA (US)

( * ) Notice: Subject to any disclaimer, the term of this patent is extended or adjusted under 35 U.S.C. 154(b) by 0 days.

(21) Appl. No.: 12/583,847

(22) Filed: Aug. 27, 2009

(65) Prior Publication Data

US 2009/0314181 A1 Dec. 24, 2009

Related U.S. Application Data

(63) Continuation of application No. 11/384,950, filed on Mar. 20, 2006, now abandoned, which is a continuation of application No. 11/059,758, filed on Aug. 15, 2005, now abandoned, which is a continuation of application No. 10/868,522, filed on Jun. 14, 2004, now abandoned, which is a continuation of application No. 10/038,786, filed on Jan. 3, 2002, now abandoned.

(60) Provisional application No. 60/259,685, filed on Jan. 4, 2001.

(51) Int. Cl.
*A61K 6/00* (2006.01)
*A61K 6/06* (2006.01)
*C04B 28/04* (2006.01)
*C04B 7/02* (2006.01)
*C04B 14/00* (2006.01)
*C04B 14/22* (2006.01)
*C04B 14/30* (2006.01)

(52) U.S. Cl. .......... 106/35; 106/712; 106/713; 106/716; 106/733; 106/736; 433/226; 433/228.1

(58) Field of Classification Search ............... 106/35, 106/711, 712, 713, 716, 733, 736; 433/226, 433/228.1
See application file for complete search history.

(56) References Cited

U.S. PATENT DOCUMENTS

| 1,432,545 | A | * | 10/1922 | Gilbert | 106/38.3 |
| 2,358,730 | A | * | 9/1944 | Nelson et al. | 264/16 |
| 5,415,547 | A | * | 5/1995 | Torabinejad et al. | 433/228.1 |
| 5,769,638 | A | * | 6/1998 | Torabinejad et al. | 433/228.1 |
| 2002/0045678 | A1 | * | 4/2002 | Lopez et al. | 523/116 |

FOREIGN PATENT DOCUMENTS

RU 20012327 C1 * 5/1994

OTHER PUBLICATIONS

Chemical Abstract No. 61:2941, abstract of an article by Leikin et al entitled "The hydration and solidification of polymer-mineral emulsions" Sb.Tr., Vses. Nauchn.-Issled. Inst. Novykh Stroit. Materialov (1963) No. 8, 57-64. [no month].*
Chemical Abstract No. 5:10932, abstract of an article by Schott entitled "Zement u Beton" (1911), 9, 793, also in "Zentr. hydraul. Zemente", 1, 195-6. [no month].*

* cited by examiner

*Primary Examiner*—Anthony J Green
(74) *Attorney, Agent, or Firm*—Douglas J. Hura; David A. Zdurne; Leana Levin

(57) ABSTRACT

A white, substantially non-iron containing dental material formed from Portland cement. The material may be a dental cement, dental restorative or the like.

17 Claims, No Drawings

DENTAL MATERIAL

RELATED APPLICATIONS

This is a continuation application of U.S. patent application Ser. No. 11/384,950, filed on Mar. 20, 2006, now abandoned, which is a continuation application of U.S. patent application Ser. No. 11/059,758, filed on Aug. 15, 2005, now abandoned, which is a continuation application of U.S. patent application Ser. No. 10/868,522 (Case TUL-LOMA-CON) filed on Jun. 14, 2004, now abandoned, which is a continuation application of U.S. patent application Ser. No. 10/038,786 (Case TUL-LOMA) filed on Jan. 3, 2002, now abandoned; which claims priority of U.S. provisional patent application Ser. No. 60/259,685 (Case TUL-LOMA) filed on Jan. 4, 2001.

TECHNICAL FIELD

The present invention is directed toward a dental material, such as a cement or a restorative material. More particularly, the invention relates to a dental material that is prepared with a Portland cement. Specifically, the invention is such a material that is substantially free from iron oxide, and which has a CaO content of from about 50 to about 75 percent by weight and an $SiO_2$ content of from about 15 to about 25 percent by weight.

BACKGROUND OF THE INVENTION

U.S. Pat. No. 5,415,547 describes a composition of cement for dental applications. However, the composition of that Portland cement is gray in color. This color is deleterious in dental applications. The grayness of the cement produces a very un-esthetic result when the cement is visible through thin tissue, such as in the smaller teeth in pedodontics, or at the gum line. According to the present invention, two types of white cement can be substituted for such a gray Portland cement: white Portland cement or calcium aluminate cement. A white cement has an advantage of being more similar in tooth color to teeth than the '547 patent. Therefore, the dark color from a conventional, gray Portland cement will not be present.

SUMMARY OF THE INVENTION

It is an object of the invention to provide a dental material.

It is another object of the invention to provide a white dental material, such as a cement, a restorative or the like.

It is an additional object of the invention to provide such a dental material that contains Portland cement.

It is a still further object of the invention to provide such a material that is substantially free of iron oxide.

A white Portland cement according to the invention contains virtually no iron, unlike the '547 patent composition which contains about 5% iron oxide. Without iron oxide, the cement will have a white color, and fall within the compositional range of Portland cements, given as follows, all percents being by weight:

61 to 70% calcia
19 to 29% silica,
5 to 15% alumina and
0 to 0.5% iron.

Preferably the material contains less than about 0.5 percent by weight of iron, based upon 100 percent by weight of the material.

PREFERRED EMBODIMENTS FOR CARRYING OUT THE INVENTION

A dental material such as a cement, restorative or the like, according to the invention, preferably has the following percentages by weight of components:

61 to 70% calcia
19 to 29% silica,
5 to 15% alumina and
0 to 0.5% iron.

Preferably the material contains less than about 0.5 percent by weight of iron, based upon 100 percent by weight of the material. More preferably, the material according to the invention is substantially free of iron oxide, meaning that it contains less than about 0.5 percent by weight of iron. Most preferably, the inventive material contains no iron. The material is visually observed to be white in color, and is therefore, more desirable in dental applications than gray-colored materials previously employed. A comparison of one embodiment of the present inventive material to known gray-colored materials is provided in TABLE I.

TABLE 1

Normalized Composition of Cement Samples

| Component | US '547 Patent | Colton Fast Set | Exemplary Inventive White Material |
|---|---|---|---|
| Calcia | 65.00 | 64.2 | 68.9 |
| Silica | 21.00 | 20.8 | 25.2 |
| Iron oxide | 5.00 | 4.3 | 0.3 |
| Alumina | 4.00 | 3.9 | 2.0 |
| Magnesia | 2.00 | 3.2 | 0.6 |
| Sulfates | 2.50 | 2.6 | 2.2 |
| Soda, potassia | <0.5 | 0.6 | 0.4 |
| Titania | — | 0.2 | 0.07 |
| Phosphorous pentoxide | — | 0.09 | 0.12 |
| Manganese oxide | — | 0.05 | 0.02 |
| Strontia | — | 0.07 | 0.13 |
| LOI | — | 1.3 | 1.0 |
| As (ppm) | — | 16•• | ND |
| Pb (ppm) | — | 4.2•• | ND |

In TABLE I, Colton Fast Set cement is commercially available from the California Portland Cement Company. Analysis was conducted by x-ray fluorescence technique, normalized excluding LOI (loss on ignition at 950° C.), and "ND" means "not detected."

Without iron oxide, the Portland cement has less of the calcium-alumino ferrite phase, as noted in Table II.

TABLE II

Composition by Phase of Cement Samples

| Component | Exemplary Prior Material | Exemplary Inventive White Material |
|---|---|---|
| $3CaO \cdot SiO_2$ | 62 | 68 |
| $2CaO \cdot SiO_2$ | 11 | 20 |
| $3CaO \cdot Al_2O_3$ | 3 | 5 |
| $4CaO \cdot Al_2O_3 \cdot Fe_2O_3$ | 13 | 1 |
| TOTAL Crystalline Phases Calculated from composition | 89 | 94 |

White Portland cements are primarily used in decorative architectural applications, although their properties are similar to that of gray cements. See Table III, where the "Exemplary Prior Cement" is manufactured according to the '547 patent, and is commercially available. The expense to exclude iron oxide from their formula makes them more expensive and more difficult to manufacture.

TABLE III

Physical Properties of Cement Samples

| Property | Exemplary Prior Cement | Exemplary Inventive White Material |
|---|---|---|
| Surface area (m²/kg) | 451 | 409 |
| Particle Size distribution | | |
| 90% finer than (μm) | 27 | 25 |
| 50% finer than (μm) | 9.4 | 9 |
| 10% finer than (μm) | 1.85 | 3 |
| Setting time, initial (min.) | 47 | 74 |
| Setting time, final (min.) | 332 | 210 |
| Compressive strength (psi) | | |
| after 1 day | 1,550 | 2,370 |
| after 3 days | 3,900 | 4,120 |
| after 7 days | 5,300 | 5,360 |
| Sulfate, weight % of cement: | | |
| as gypsum, CaSO$_4$•2H$_2$O | 0.2 | not detected |
| (K$_2$SO$_4$•CaSO$_4$•H2O) | | |
| % plaster (hemi-hydrate) (calculated as % SO3) | 86 | 50 |

Calcium aluminate cements can be used instead of a white Portland cement. The calcium aluminate cements contain from about 32 to about 57 weight percent alumina, and are clearly outside the '547 patented composition. The silica content is usually less than 6 weight percent, the iron content is less than 20 weight percent (especially low when white cement is needed), and the titania content is also less than 2 percent. Titania makes the cement whiter.

The calcium aluminate cements generally set in one-half the time of Portland cements. However, a very fast set may be achieved by combining calcium aluminate and Portland cements. A "flash" set phenomena can occur where the setting time is reduced to less than 1 hour when a 50/50 mixture of calcium aluminate and Portland cements is made. TABLE IV shows that calcium aluminate cements set more quickly than do Portland cements. In this graph, the final set time is about 4.25 hours for a calcium aluminate cement, and about 7 hours for a Portland cement.

Calcium aluminate cements can be stronger than Portland cements, in some cases twice as strong when fully set. Furthermore, calcium aluminate cement develops its strength sooner. Calcium aluminate cements an achieve 50% of their total strength in less than 1 day whereas a portland cement may require between 1 and 6 days to achieve 50% of their final strength.

Calcium aluminate cements are not usually used in applications that hover around ambient temperature; they are usually used for refractory applications. Below 27° C., an unstable hydrate is formed: CaO.Al$_2$O$_3$.10H$_2$O. Above 27° C. these hydrates release their water in a process called conversion and form the stable hydrates of 2CaO.Al$_2$O$_3$.8H$_2$O, 3CaO.Al$_2$O$_3$.6H$_2$O and Al$_2$O$_3$.3H$_2$O. Unfortunately this process creates pores that reduce the strength. We have a unique situation in dentistry with using calcium aluminate cements in the body where the temperature is constant and above 27° C. Therefore, a stable hydrate can be formed that does not convert. High strengths and quick setting scan be achieved without risk of conversion.

Sample compositions of two inventive calcium aluminate cements are given in Table V, compared to a gray and two inventive white Portland cements.

TABLE V

Comparison of Cement Compositions

| | Type Cement | | | | |
|---|---|---|---|---|---|
| Oxide | Portland Colton Fast Set | Portland White | Portland White | Calcium Aluminate | Calcium Aluminate |
| Calcia | 64.2 | 66.3 | 68.2 | 29.8 | 33.9 |
| Alumina | 3.9 | 4.3 | 1.9 | 56.5 | 53.0 |
| Silica | 20.8 | 21.9 | 24.8 | 2.9 | 2.2 |
| Iron oxide | 4.3 | 0.3 | 0.4 | 1.3 | 1.1 |
| Magnesia | 3.2 | 2.0 | 0.5 | 0.4 | 0.7 |
| Sulfate | 2.5 | 3.3 | 2.2 | 0.2 | 0.0 |
| Potassia | 0.3 | 0.3 | 0.1 | 0.1 | 0.2 |
| Soda | 0.3 | 0.1 | 0.1 | 4.8 | 4.7 |
| Strontia | 0.1 | 0.1 | 0.1 | 0.0 | 0.0 |
| Manganese oxide | 0.1 | 0.0 | 0.0 | 0.0 | 0.0 |
| Phos. Pentoxide | 0.1 | 0.1 | 0.1 | 0.1 | 0.0 |
| Chlorine | | 0.0 | 0.0 | 0.1 | 0.0 |
| Scandia | | 0.0 | 0.0 | 0.1 | 0.1 |
| Titania | 0.2 | 0.2 | 0.1 | 2.1 | 2.2 |
| Bromine | | 0.0 | 0.0 | 0.1 | 0.2 |
| Chromia | | 0.0 | 0.0 | 0.0 | 0.1 |
| Zirconia | | 0.0 | 0.0 | 0.1 | 0.0 |
| Silver oxide | | 0.0 | 0.0 | 1.0 | 1.1 |
| Platinum oxide | | 0.0 | 0.0 | 0.1 | 0.0 |
| TOTAL | 100.0 | 100.0 | 100.0 | 100.0 | 100.0 |

According to the invention, fluoride can also be added to a Portland cement in the form of calcium fluoride. Additions of 1.7 wt % fluorine in the cement before firing, increase the strength (at 28 days of setting) about 10%. The fluoride may or may not be released from such a cement.

Some dental applications do not require high radiopacity, such as pulp capping. The sealing and capacity for dentinal bridge formation are more important than radiopacity for use of the material in a thin layer required for pulp capping. For added effectiveness in some dental applications, a cement can be made radiopaque. For instance, with the addition of 20 wt % bismuth oxide, the mixture will have a radiopacity equal to 3 mm of aluminum at a cement thickness of 1 mm. The gray and white portland cements have equal radiopacity, 3 mm of Al equivalent, at 1 mm of cement thickness, when blended with 20% bismuth oxide. As much as 40% bismuth oxide can be added to the mixture, however, the bismuth oxide slows the setting and strength development. The bismuth oxide imparts a pale yellow color to the mixture because the bismuth oxide is yellow-colored.

Another radiopacifier can be blended with the cement. For instance, a radiopaque glass used for dental composites can be mixed with portland cement, as an alternative to bismuth oxide. The color of the mixture is white. A glass such as Corning 7724 or 7726 can be used. Such glasses are covered under U.S. Pat. Nos. 4,920,082 or 4,775,646, respectively. If a fluoride-releasing glass is used, this mixture would be radiopaque and release fluoride ions. The fluoride release would help prevent internal resorption or cervical decay.

A third radiopaque addition would be barium sulfate instead of bismuth oxide. The barium sulfate is not soluble in water; therefore it would not be a toxic heavy metal compound. This material is white and would also avoid gray coloration of the mixture.

Another addition to cement is Bioglass. Bioglass, a patented formula of glass, is known to be biologically active, and encourage bone growth (see U.S. Pat. No. 4,232,972). Its formula is within this compositional range (all percentages being by weight (wt %)):

| | |
|---|---|
| Silica | 40-62% |
| Soda | 10-32% |
| Calcia | 10-32% |
| Phosphorous pentoxide | 0-12% |
| Calcium fluoride | 0-18% and |
| Boron oxide | 0-20%. |

The Bioglass can be added as coarse powder, about 170 to 140-mesh size. The large, coarse form of the glass has been found to be more conducive to bone growth than a finer size. Bioglass particles could be used as an "aggregate" in a portland cement and create a concrete. Bioglass (see U.S. Pat. No. 4,775,646) is a white powder, and would not color a mixture with white cement. This would be of most interest for filling bony defects or root-end filling where bone re-growth is important. Hench has patented the mixture of Bioglass and cement. See U.S. Pat. No. 4,775,646 to L. Hench et. al for a fluoride-containing Bioglass. U.S. Pat. No. 4,171,544 to L. Hench et. al for bonding to bone with a high surface area porous, silica-rich surface. This teaches about portland cement for BONDING (not as the restorative for) dental implants, and cement mixed with a biologically active glass.

Other compositions of cement can be considered to create a white cement, as long as they do not include iron oxide. For instance, barium oxide can be partially or wholly substituted for calcium oxide. This is a new ingredient, not specified in the first Torabinejad patent (U.S. Pat. No. 5,415,547). This would create a cement that is inherently radiopaque and needs no further additions.

The fineness of the cement also affects its usefulness in dentistry. For instance the Torabinejad patent refers to cements of Type 3, a relatively fine cement having a surface area of 450 to 550 $m^2/kg$. However, such cements are perceived as grainy or sandy by dentists, having lesser quality, and less packable into fine orifices. The surface area measurement gives a general indication of the fineness of the powder, but does not adequately characterize the distribution of the powder particles sizes.

Two approaches can be followed to improve the performance of such dental materials: removal of coarse particles, or reduction in the average particle size. The removal of coarse particles can be achieved by sieving or air elutriation. The particle size reduction can be achieved by milling processes such as ball milling, air attrition, or attrition milling.

Finer cements are more suitable for either a root canal sealing material or a root canal obturation material. The use of a cement with a surface areas of about 1,000 $m^2/kg$ allows it to be easily filled in a root canal, including lateral canals. We tested such a cement for a root canal sealer and found it preferable to a cement have a lower surface area. Furthermore, the removal of particles coarser than 400 mesh (44 μm) improved the handling of the gray cement used in the commercially available ProRoot MTA material. This process increased the measured surface area from 454 to 509 $m^2/kg$.

Therefore, it is apparent that a dental material according to the invention as described above, is useful in meeting the stated objectives of the invention. It will be understood that amount of various components, can be varied and still fall within the scope of the invention. Similarly, specific formulation components as provided above are merely exemplary and other components similar or otherwise are also within the scope of the invention. The scope of the invention will be determined only by the claims.

What is claimed is:

1. A dental material comprising Portland cement and which contains:
   from about 50 to about 75 weight percent calcia;
   from about 15 to about 29 weight percent silica;
   alumina;
   less than about 0.5 percent by weight of iron oxide; and
   a radiopacifier
   based upon 100 percent by weight of the material.

2. The dental material as in claim 1 which is white in color.

3. The dental material as in claim 1, wherein the radiopacifier is present in an amount of less than 40 weight percent of the material.

4. The dental material as in claim 3, wherein the radiopacifier is bismuth oxide, fluoride releasing glass, or barium sulfate.

5. The dental material as in claim 1, wherein the radiopacifier is bismuth oxide, fluoride releasing glass, or barium sulfate.

6. The dental material as in claim 3, wherein the radiopacifier is bismuth oxide.

7. The dental material as in claim 1, wherein the radiopacifier is bismuth oxide.

8. The dental material as in claim 1, wherein the material has a radiopacity equal to 3 mm of aluminum at a cement thickness of 1 mm.

9. The dental material as in claim 3, wherein the material is free of particles coarser than 400 mesh (44 μm).

10. The dental material as in claim 1, wherein alumina is present from 2 to about 15 weight percent of the material.

11. The dental material as in claim 1, wherein alumina is present from about 5 to about 15 weight percent of the material.

12. The dental material as in claim 1, wherein:
   a) the radiopacifier is present in an amount of less than 40 weight percent of the material;
   b) the radiopacifier is bismuth oxide, fluoride releasing glass, or barium sulfate; and
   c) the material is free of particles coarser than 400 mesh (44 μm).

13. The dental material as in claim 12, wherein the material has a radiopacity equal to 3 mm of aluminum at a cement thickness of 1 mm.

14. The dental material as in claim 13, wherein the radiopacifier is bismuth oxide.

15. The dental material as in claim 14, wherein silica is present from about 15 to about 25 weight percent of the material.

16. The dental material as in claim 15, wherein alumina, is present from 2 to about 15 weight percent of the material.

17. The dental material as in claim 16, wherein calcia is present from about 61 to about 70 weight percent of the material.

* * * * *